(12) United States Patent
Heimann et al.

(10) Patent No.: US 6,888,109 B2
(45) Date of Patent: May 3, 2005

(54) HEATING DEVICE

(75) Inventors: Detlef Heimann, Gerlingen (DE); Torsten Handler, Stuttgart (DE); Lothar Diehl, Stuttgart (DE); Dieter Lindauer, Muehlacker (DE); Dietmar Seizinger, Vaihingen/Enz (DE)

(73) Assignee: Robert Bosch GmbH, Stuttgart (DE)

( * ) Notice: Subject to any disclaimer, the term of this patent is extended or adjusted under 35 U.S.C. 154(b) by 208 days.

(21) Appl. No.: 10/182,229
(22) PCT Filed: Nov. 13, 2001
(86) PCT No.: PCT/DE01/04252
  § 371 (c)(1),
  (2), (4) Date: Oct. 18, 2002
(87) PCT Pub. No.: WO02/44701
  PCT Pub. Date: Jun. 6, 2002

(65) Prior Publication Data
  US 2004/0031786 A1 Feb. 19, 2004

(30) Foreign Application Priority Data
  Nov. 25, 2000 (DE) .......................................... 100 58 643

(51) Int. Cl.⁷ ................................................. H05B 3/02
(52) U.S. Cl. ..................... 219/484; 219/543; 219/497; 204/424; 204/425; 204/426; 204/427; 204/408
(58) Field of Search ................................ 219/484, 543, 219/497; 204/424–8, 429, 408

(56) References Cited

U.S. PATENT DOCUMENTS 4,859,307 A  *  8/1989  Nishizawa et al. ......... 204/425

FOREIGN PATENT DOCUMENTS

DE          198 34 276        2/2000

* cited by examiner

*Primary Examiner*—Shawntina Fuqua
(74) *Attorney, Agent, or Firm*—Kenyon & Kenyon

(57) ABSTRACT

A heating device for a gas sensor, in particular for use in the exhaust gas analysis of internal combustion engines, including a heating element having an electrical resistor layer. The heating element is embedded in a first insulation which in turn is surrounded, at least in part, by a second insulation. The first and the second insulation have different porosities.

32 Claims, 1 Drawing Sheet

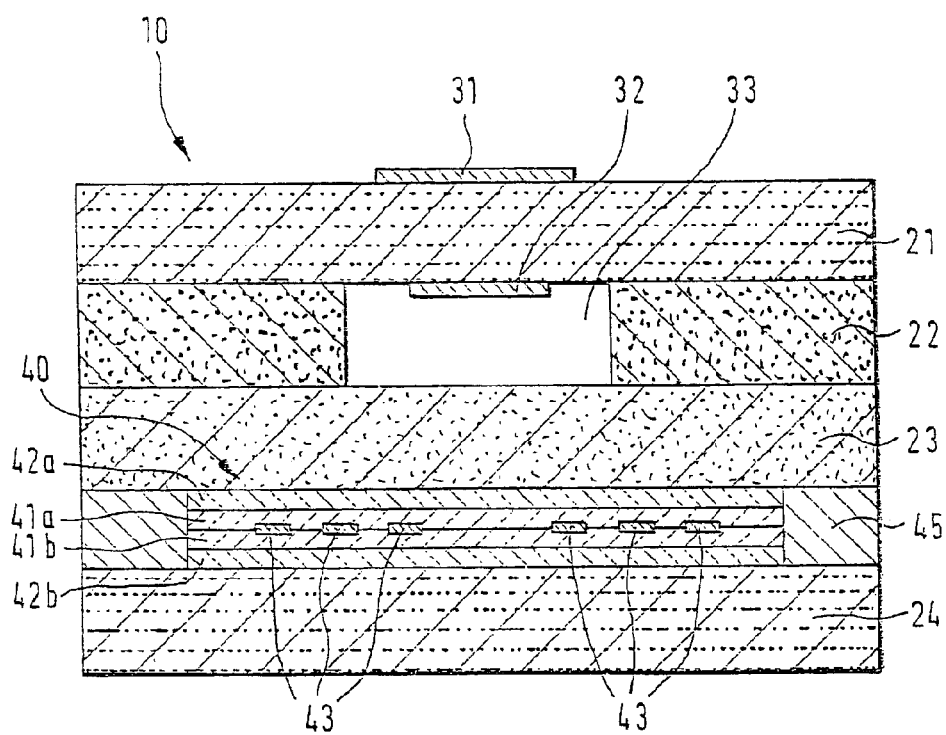

HEATING DEVICE

FIELD OF THE INVENTION

The present invention relates to a heating device for a gas sensor.

BACKGROUND INFORMATION

Such a heating device for heating a sensor element used in a gas sensor for exhaust gas analysis of internal combustion engines, is referred to in German Published Patent Application No. 198 34 276, for example. The sensor element includes solid electrolyte layers, and electrodes, as well as a heating device having a layered configuration. The heating device is arranged on a solid electrolyte layer or between one solid electrolyte layer and another solid electrolyte layer. The heating device includes a heating element in the form of an electrical resistor layer, for example, as well as an insulation in which the heating element is embedded. The insulation has a uniform material composition and a uniform structure, in particular with regard to the porosity. The insulation serves the purpose of electrically insulating the heating element against the solid electrolyte layers and the electrodes, thus with regard to both electron and ion conduction, so that the operation of the heating device does not affect the function of the sensor element.

The heating device is manufactured by applying a lower layer of insulation, the heating element, and an upper layer of insulation, using thin-layer or thick-layer techniques, to a green foil, i.e., an unsintered ceramic foil. Subsequently, the green foil with the heating device printed on it and other green foils, with electrodes optionally printed on them, for example, are laminated and sintered.

The insulation frequently has a porous configuration. The porosity of the insulation is achieved by adding a pore former before sintering. The pore former burns during sintering and thus creates a porous structure. The porosity is adjusted through the added amount of pore former, for example glass carbon.

An insulation having a higher porosity may be disadvantageous, because leak currents may occur during operation. These leak currents develop due to contaminations within the insulation, for example by volatilization of a metallic component of the heating element, platinum for example, or due to moisture in the heating device. The higher the porosity of the insulation, the easier contaminants may penetrate the insulation and deposit in the pores of the insulation, and the higher the leak current.

On the other hand, an insulation having a lower porosity has the disadvantage that with a decreasing porosity the elasticity of the insulation decreases, resulting in increased susceptibility to cracking. This may result in an interruption of the heating element's operation. The risk of crack formation is also given if moisture penetrates into the heating device, for example, via a contact of the heating element. The lower the porosity of the insulation, the less volume is available to absorb the gas developing during heating-up and the higher the susceptibility to cracking.

In the heating devices of other prior systems including only one insulation with a uniform porosity, either the discussed disadvantages of an insulation having a higher porosity, or the disadvantages of an insulation having a lower porosity occur.

SUMMARY OF THE INVENTION

The exemplary heating device according to the present invention may provide the advantage that leak currents between the heating element and the electrodes are largely prevented, and also the risk of cracks in the heating element is greatly reduced.

If the heating element is surrounded by a first and a second insulation having different porosities, the risk of crack formation is reduced due to the insulation having the higher porosity and thus the higher elasticity, while the leak currents are greatly reduced due to the insulation having the lower porosity.

If the heating element is embedded in a first insulation having a higher porosity than a second insulation surrounding the first insulation, the formation of cracks is particularly effectively prevented, if, for example, moisture may penetrate into the heating element of the heating device via a contact.

It is advantageous, in particular, to provide the first insulation with an open porosity. In the case of an open porosity, the pores are linked with each other, so that an insulation having an open porosity is gas-permeable. In a first insulation having an open porosity, crack formation is prevented even if larger amounts of moisture penetrate into the heating device. Since the pores are linked with each other, they are able to absorb larger amounts of the evaporating liquid.

Furthermore, it is particularly advantageous to provide the second insulation with a closed porosity. In the case of a closed porosity the pores are closed, i.e., they are not linked with each other at least over wider areas. An insulation having a closed porosity is therefore gas-tight. In a second insulation having a closed porosity, it is prevented that contaminants penetrate into the second insulation, so that the leak current is particularly effectively reduced.

If the first insulation-surrounding the heating element has a lower porosity than the second insulation, the volatilization of the metallic component of the heating element is particularly effectively prevented. Thereby, it is achieved that contractions in the cross section area of the heating element are avoided, which might otherwise occur during longer operating times due to volatilization. This arrangement, where the second insulation is the more porous layer, is advantageous in particular in applications where no or only little moisture is to be expected in the heating element.

An exemplary embodiment of the present invention is illustrated in the drawing and is explained in the following description.

BRIEF DESCRIPTION OF THE DRAWING

FIG. 1 shows a cross section of an exemplary embodiment of a planar sensor element including an exemplary heating device according to the present invention.

DETAILED DESCRIPTION

As an exemplary embodiment of the present invention, the figure shows a planar sensor element 10, constructed in layers, including a first, second, third, and fourth solid electrolyte layer 21, 22, 23, 24, made of an ion-conductive material. First electrode 31, exposed to a measuring gas, is arranged on first solid electrolyte layer 21. Second electrode 32, exposed to a reference gas in reference gas channel 33, is arranged on solid electrolyte layer 21 on the side facing away from electrode 31. Reference gas channel 33 is introduced in second solid electrolyte layer 22 and is connected to a reference gas atmosphere (not shown) arranged outside of sensor element 10.

First and second electrode 31, 32, as well as first solid electrolyte layer 21 form an electrochemical cell, which is operated potentiometrically, for example. If the oxygen partial pressures of the measuring gas and the reference gas are different, a Nernst voltage with which the oxygen partial pressure of the measuring gas may be determined is applied between first and second electrode 31, 32.

Since the ion-conductivity of the solid electrolyte is temperature-sensitive, it is necessary to heat up sensor element 10 to a uniform temperature. To achieve this, heating device 40, laterally surrounded by sealing frame 45, is provided between third and fourth solid electrolyte layer 23, 24.

Heating device 40 includes a heating element 43, which is made up of a resistor layer containing platinum. Heating element 43 is embedded between upper layer 41a and lower layer 41b of first insulation 41. Insulation 41 and heat element 43 are arranged between upper layer 42a and lower layer 42b of a second insulation 42. $Al_2O_3$ is a component of first and second insulation 41, 42. The manufacture of such insulations is known to those skilled in the art and is not described in detail.

In a first exemplary embodiment, first insulation 41 has a porosity of 8% by volume after sintering and second insulation has a porosity of 3% by volume after sintering. A proportion of 5% by weight of pore former, based on the $Al_2O_3$ component in the non-sintered state, is added to first insulation 41 and a proportion of 2% by weight of pore former, also based on the $Al_2O_3$ component in the unsintered state is added to second insulation 42.

The amount of pore former required for a specific porosity in sintered insulations 41, 42 may vary, depending on the course of the sintering operation, the particle size, and the chemical composition of the layers to be sintered. However, a suitable proportion of pore former may be experimentally determined for a given combination of initial variables.

Carbon is used as pore former. Flame carbon black 101 made by Degussa has been found to be particularly suitable, because it contains particularly fine and uniform particles. The median particle size of the pore former may be in the range of 0.01 µm to 1 µm, for example.

Depending on the field of application, other porosities may be selected. Therefore, in the case of an increased susceptibility to cracking, a higher porosity may be selected for insulations 41, 42. For applications requiring a particularly low leak current, a lower porosity may be selected for insulations 41, 42 accordingly. In general, a porosity of 5% to 16% by volume for first insulation 41, and a porosity of 1.5% to 5% by volume for insulation 42, has proved suitable. In unsintered first insulation 41, this corresponds to a pore former proportion of 3% to 10% by weight, based on the $Al_2O_3$ component and in unsintered second insulation 42 it corresponds to a pore former proportion of 1% to 3% by weight, also based on the $Al_2O_3$ component.

In a second exemplary embodiment, the porosity of the first insulation corresponds to the porosity of second insulation 42 in the first exemplary embodiment, and the porosity of the second insulation corresponds to the porosity of first insulation 41 in the first exemplary embodiment.

In a further exemplary embodiment (not shown), the heating element, as well as the first and second insulations are at least in part surrounded by at least one additional insulation, whose porosity differs from the porosity of the second insulation. The porosity of the other insulation may be the same as the porosity of the first insulation.

The exemplary heating device according to the present invention is naturally transferrable to other types of sensors, a broad-band λ probe, for example.

What is claimed is:

1. A heating device for a gas sensor for use in analyzing exhaust gas of an internal combustion engine, the heating device comprising:

a heating element that includes an electrical resistor layer and that is electrically insulated;

a first insulation, wherein the heating element is embedded therein; and a second insulation at least partially surrounding the first insulation, wherein the first insulation and the second insulation have different porosities.

2. The heating device of claim 1, wherein the first insulation has a higher porosity than the second insulation.

3. The heating device of claim 2, wherein the first insulation has an open porosity.

4. The heating device of claim 2, wherein the second insulation has a closed porosity.

5. The heating device of claim 2, wherein the first insulation has a porosity of 5% to 16% by volume.

6. The heating device of claim 2, wherein the first insulation has a porosity of 8% by volume in a sintered state.

7. The heating device of claim 2, wherein the second insulation has a porosity of 1.5% to 5% by volume.

8. The heating device of claim 2, wherein the second insulation has a porosity of 3% by volume in a sintered state.

9. The heating device of claim 2, wherein at least one of the first insulation and the second insulation includes $Al_2O_3$.

10. The heating device of claim 9, wherein, in an unsintered state, the first insulation has 3% to 10% by weight based on the $Al_2O_3$.

11. The heating device of claim 10, wherein the first insulation has 5% by weight of a pore former.

12. The heating device of claim 9, wherein, in an unsintered state, the second insulation has 1% to 3% by weight based on the $Al_2O_3$.

13. The heating device of claim 12, wherein the second insulation has 2% by weight of a pore former.

14. The heating device of claim 11, wherein a flame carbon black having a median particle size in a range of 0.01 µm to 1 µm is used as the pore former.

15. The heating device of claim 13, wherein a flame carbon black having a median particle size in a range of 0.01 µm to 1 µm is used as the pore former.

16. The heating device of claim 2, wherein the second insulation is at least partially surrounded by at least one additional insulation that has a higher porosity than the second insulation.

17. The heating device of claim 1, wherein the first insulation has a lower porosity than the second insulation.

18. The heating device of claim 17, wherein the first insulation has a closed porosity.

19. The heating device of claim 17, wherein the second insulation has an open porosity.

20. The heating device of claim 17, wherein the first insulation has a porosity of 1.5% to 5% by volume in a sintered state.

21. The heating device of claim 20, wherein the first insulation has a porosity of 3% by volume.

22. The heating device of claim 17, wherein the second insulation has a porosity of 5% to 16% by volume in a sintered state.

23. The heating device of claim 22, wherein the second insulation has a porosity of 8% by volume.

24. The heating device of claim 14, wherein at least one of the first insulation and the second insulation includes $Al_2O_3$.

25. The heating device of claim 24, wherein the first insulation has 1% to 3% by weight based on $Al_2O_3$ in an unsintered state.

26. The heating device of claim 25, wherein the first insulation has 2% by weight of a pore former.

27. The heating device of claim 24, wherein the second insulation has 3% to 10% by weight based on $Al_2O_3$ in an unsintered state.

28. The heating device of claim 27, wherein the second insulation has 5% by weight of a pore former.

29. The heating device of claim 17, wherein the second insulation is at least partially surrounded by at least one additional insulation that has a lower porosity than the second insulation.

30. The heating device of claim 1, wherein the heating device is arranged inside a planar sensor element having a layered configuration and located in a gas sensor, between a first solid electrolyte layer and a second solid electrolyte layer.

31. The heating device of claim 1, wherein the heating device is laterally surrounded by a sealing frame made from an ion-conductive material.

32. The heating device of claim 1, wherein the second insulation is at least partially surrounded by at least one additional insulation.

* * * * *

UNITED STATES PATENT AND TRADEMARK OFFICE
CERTIFICATE OF CORRECTION

PATENT NO.    : 6,888,109 B2
DATED         : May 3, 2005
INVENTOR(S)   : Heimann et al.

It is certified that error appears in the above-identified patent and that said Letters Patent is hereby corrected as shown below:

<u>Column 4,</u>
Line 65, change "device of claim 14," to -- device of claim 17, --.

Signed and Sealed this

Thirteenth Day of December, 2005

JON W. DUDAS
*Director of the United States Patent and Trademark Office*